(12) United States Patent
Mann

(10) Patent No.: US 6,521,266 B1
(45) Date of Patent: Feb. 18, 2003

(54) COMPOSITION FOR GROWTH HORMONE PRODUCTION AND RELEASE, APPETITE SUPPRESSION, AND METHODS RELATED THERETO

(76) Inventor: Morris A. Mann, 21669 N. 57th Ave., Glendale, AZ (US) 85308

( * ) Notice: Subject to any disclaimer, the term of this patent is extended or adjusted under 35 U.S.C. 154(b) by 0 days.

(21) Appl. No.: 09/669,403

(22) Filed: Sep. 23, 2000

Related U.S. Application Data

(63) Continuation of application No. 60/191,202, filed on Mar. 22, 2000
(60) Provisional application No. 60/156,005, filed on Sep. 23, 1999.

(51) Int. Cl.$^7$ .................. A01N 65/00; A01N 43/62; A01N 43/16; A61K 35/78
(52) U.S. Cl. .................. 424/725; 514/219; 514/458; 424/730; 424/752
(58) Field of Search .................. 424/184.1, 278.1, 424/725, 195.1, 730, 752; 514/219, 458; 930/250

(56) References Cited

U.S. PATENT DOCUMENTS

| | | | | |
|---|---|---|---|---|
| 4,711,897 A | * | 12/1987 | Lindsey et al. | 514/665 |
| 5,597,797 A | * | 1/1997 | Clark | 514/12 |
| 5,723,106 A | * | 3/1998 | Buch et al. | 424/49 |
| 5,942,244 A | * | 8/1999 | Friedman et al. | 424/435 |
| 6,261,589 B1 | * | 7/2001 | Pearson et al. | 424/439 |

OTHER PUBLICATIONS

PDR for Herbal Medicines; Montvale NJ, (1998) First Edition, pp. 1184–1185.*

* cited by examiner

*Primary Examiner*—Christopher R. Tate
*Assistant Examiner*—Patricia Patten
(74) *Attorney, Agent, or Firm*—The Halvorson Law Firm

(57) ABSTRACT

A method for enhancing growth hormone production and release, for appetite suppression, or both, in a subject in need thereof. The method comprises administering to the subject an effective amount of a first composition, wherein the first composition increases cholinergic tone and growth hormone synthesis, and the second composition inhibits somatostatin. The first composition may be a combination of an acetylcholinesterase inhibitor and Vitamin E D-α-succinate, whereas the second composition may be a salt of cysteamine and an alkali buffer, or may be pantothenic acid and an alkali metal salt. A two-part composition comprising the first and second compositions as also disclosed.

4 Claims, No Drawings

COMPOSITION FOR GROWTH HORMONE PRODUCTION AND RELEASE, APPETITE SUPPRESSION, AND METHODS RELATED THERETO

This application is a continuation application of previously filed provisional application Ser. No. 60/191,202, filed on Mar. 22, 2000 entitled "COMPOSITION FOR GROWTH HORMONE PRODUCTION AND RELEASE, APPETITE SUPPRESSION, AND METHODS RELATED THERETO", which was a continuation in part of previously filed provisional application Ser. No. 60/156,005, filed on Sep. 23, 1999 entitled "COMPOSITION FOR GROWTH HORMONE PRODUCTION AND RELEASE, APPETITE SUPPRESSION, AND METHODS RELATED THERETO".

TECHNICAL FIELD

The present invention is generally directed to methods and compositions that enhance growth hormone production and release, and which have been found to suppresses appetite, in human subjects.

BACKGROUND OF THE INVENTION

Growth hormone plays an important role in the physiology of warm-blooded animals, including humans. To date, there have been several methods developed to increase growth hormone levels within the body to influence a disease state such as, for example, pituitary dwarfism, or to facilitate healing after trauma associated with burns, surgery, etc. Relatedly, it has been noted that growth hormone levels within the body markedly decrease after puberty, and gradually decline thereafter throughout life. It has also been noted that growth hormone supplementation in elderly individuals cause physiological changes consistent with rejuvenation. Accordingly, growth hormone supplementation is considered by many to be highly advantageous.

Additionally, there are several known compounds which are considered to be growth hormone secretogogues, but these compounds do not necessarily promote growth hormone synthesis. There are also several known compounds which promote growth hormone synthesis, but these compounds do not necessarily induce the release or secretion of the growth hormone. Moreover, due to the large size and fragility associated with growth hormone molecules (191 peptide residues), growth hormone (and similar agents) is generally administered into the body via an injection. There are, however, several shortcomings associated with systemic delivery by injection, shortcomings such as increased risk of infection at the site of delivery.

Accordingly, there is a need in the art for a composition that enhances growth hormone production and release within a subject, as well as to methods relating thereto. The present invention fulfills these needs and provides for further related advantages.

SUMMARY OF THE INVENTION

In brief, the present invention is generally directed to compositions and methods for enhancing growth hormone production and release, in a subject so as to effectuate rejuvenation. In the practice of this invention, it has also been found that such compositions simultaneously serve to suppress appetite.

In one embodiment, a method for enhancing growth hormone production and release in a subject so as to effectuate rejuvenation and appetite suppression is disclosed. The method comprises the steps of administering to a subject in need thereof an effective amount of a first composition, wherein the first composition increases cholinergic tone above a baseline level; and administering to the subject an effective amount of a second composition, wherein the second composition decreases somatostatin below a baseline level. The first composition may be a combination of an acetylcholinesterase inhibitor and Vitamin E α-D-succinate, whereas the second composition may be a combination of a salt of cysteamine (e.g., cysteamine hydrochloride salt) and an alkali buffer. Alternatively, the second composition may be a combination of pantothenic acid and an alkali metal salt, as well as a reducing agent as an optional component. It is to be understood that other forms of cysteamine, including the base, may also be used.

In another embodiment, a kit useful for enhancing growth hormone production and release so as to effectuate rejuvenation and appetite suppression is disclosed. The kit comprises a first composition and a second composition, wherein first composition comprises an acetylcholinesterase inhibitor and Vitamin E α-D-succinate, whereas the second composition is a salt of cysteamine (e.g., cysteamine hydrochloride salt) and an alkali buffer, or pantothenic acid and an alkali metal salt. In a more specific embodiment, the first composition comprises choline bitartrate in an amount ranging from 0.01 to 95% by weight; dimethylaminoethanol in an amount ranging from 0.01 to 85% by weight; Vitamin E α-D-succinate in an amount ranging from 0.01 o 85% by weight; gingko biloba 24% gingosides in an amount ranging from 0.001 to 30% by weight; Huperzine A in an amount ranging from 0.000000001 to 5% by weight; and 5-Hydroxytryptophan in an amount ranging from 0.001 to 30% by weight; and wherein the second composition comprises cysteamine HCL in an amount ranging from 0.001 to 90% by weight. In an alternative embodiment, the second composition comprises calcium pantothenate in an amount ranging from 0.01 to 99% by weight; magnesium phosphate tribasic in an amount ranging from 0.01 to 99% by weight; magnesium phosphate tribasic in an amount ranging from 0.1 to 85% by weight; magnesium sulfite in an amount ranging from 0.1 to 85% by weight; and citric acid in an amount ranging from 0.01 to 95% by weight of the second composition.

The present invention is also directed to a method for suppressing appetite within a subject, comprising the steps of orally administering an effective amount of the kit of this invention.

These and other aspects of this invention will be evident upon reference to the following detailed description.

DETAILED DESCRIPTION OF THE INVENTION

The present invention is generally directed to compositions and methods for enhancing growth hormone production and release in a subject so as to effectuate rejuvenation and appetite suppression. Although many specific details associated with certain aspects of the present invention are set forth below, those skilled in the art of pharmacology, and especially neuropharmacology, will recognize that the present invention may have additional embodiments, or that the invention may be practiced without several of the details disclosed herein.

As noted above, it is known that growth hormone plays a vital role in human physiology, and numerous methods have been developed to increase growth hormone levels within a human body so as to influence a variety of disease states. It is also known that growth hormone levels decrease after puberty, and continue to gradually decline throughout life, and that growth hormone supplementation in elderly individuals causes changes consistent with rejuvenation. However, because of the size and fragility of the growth hormone molecule, it must be administered by injection. Accordingly, an orally available composition capable of enhancing growth hormone production and release is needed.

The present invention provides an orally administered composition for enhancing growth hormone production and release, and methods related thereto. In addition, it has been surprisingly found that the composition of this invention also serves to suppress appetite in human subjects, which is a desirable attribute in and of itself.

succinate increases growth hormone synthesis in vitro. Similarly, melatonin will also increase growth hormone synthesis. Unfortunately, there may be a negative feedback on melatonin synthesis in vivo when melatonin is exogenously administered. However, there are amino acids, such as tryptophan and 5-hydroxytryptophan which will increase melatonin synthesis in vivo with chronic administration.

In view of the foregoing, it has been discovered that the first part of the kit of this invention—that is, the part for enhancing cholinergic tone and growth hormone synthesis—may include (as a representative embodiment of this invention) those substances identified in Table 1 below.

TABLE 1

ENCAPSULATED FORMULA CONTAINING SUBSTANCES FOR ORAL ADMINISTRATION TO ENHANCE CHOLINERGIC TONE AND GROWTH HORMONE SYNTHESIS

|  | Mg/capsule | % | Range |
| --- | --- | --- | --- |
| Choline bitartrate | 200 mg | 42 | 0.01–95 |
| Dimethylamnoethanol | 100 mg | 21 | 0.01–85 |
| Vitamin E α-D-succinate | 100 im = 100 mg | 21 | 0.01–85 |
| Gingko biloba 24% ginkosides | 25 mg | 5.2 | 0.001–30 |
| St. John's Wort (0.3% hypericum) | 25 mg | 5.2 | 0.001–30 |
| Huperzine A | 35 mg | 0.0000073 | 0.000000001–5 |
| 5-Hydroxytryptophan | 25 mg | 0.1999927 | 0.001–30 |

The composition of this invention is a kit formulation, wherein the first part of the composition enhances (1) cholinergic tone and (2) growth hormone synthesis, and wherein the second part of the composition inhibits (3) somatostatin production. Because of the importance associated with the above, each is more fully discussed below.

Increasing Cholinergic Tone

Substances that will increase acetylcholine production and release tend to result in an increase in cholinergic tone above baseline. These substances include, but are not limited to various choline-containing compounds, such as choline bitartrate or phosphatidyl choline; acetylcholine precursors, such as dimethylaminoethanol and congeners related thereto. Substances that increase blood flow in the cerebral cortex are known to increase acetylcholine levels. These substances include, but are not limited to: ginkgo biloba with gincosides assayed at 24% of total weight, niacin, papaverine, hydergine and other ergot alkaloids, etc. Other substances known to increase acetylcholine release include a variety of cholinergic agents, such as pyridostigmine, etc. However, for the purpose of the present invention, an acetylcholinesterase inhibitor is preferred. The Chinese moss derivative huperzine A, which is known to enhance cognition, also affects cholinergic tone. This substance, in conjunction with substances that increase the overall levels of acetylcholine, results in a substantial increase of acetylcholine levels above baseline. Other substances that increase acetylcholine levels include hypericum (St. John's Wort) and S-adenosulmethionine. Seemingly, the antidepressant effects of these two compositions are partially related to their ability to increase acetylchie levels. As is appreciated by those skilled in the art, irreversible acetylcholine esterase inhibitors, such as malathion will increase acetylcholine levels. Unfortunately, these agents are difficult to administer therapeutically because of their narrow margin of safety.

Increasing Growth Hormone Synthesis

Several compounds will enhance growth hormone synthesis. It was recently discovered that Vitamin E α-D-

Inhibiting Somatostatin Synthesis

There are a limited number of substances that will inhibit somatostatin production. The most potent of these is cysteamine. Unfortunately, this molecule is unstable in air and therefore the salt is used for oral administration in the context of this invention. This substance has been used extensively in agriculture to decrease the time it takes to bring livestock and chickens to market. Unfortunately, this substance is from the chemical class known as mercaptans, which are among the worst smelling and tasting chemicals known to man. As such, and to avoid acid hydrolysis in the gut, cysteamine may be formulated as a readily absorbable liquid preparation.

Accordingly, in view of the foregoing, it has been discovered that the second part of the kit of this invention—that is, the part for inhibiting somatostatin synthesis—may include (as representative embodiments of this invention) those substances identified in Table 2a (liquid form) or Table 2B (capsule form).

TABLE 2A

SOMATOSTATIN INHIBITING AND APPETITE-SUPPRESSING COMPOSITION

| Liquid | % | Range |
| --- | --- | --- |
| Alcohol | 20 | .1–99 |
| Glycerin | 78.7 | .1–99 |
| Cysteamine HCL | .1 | .001–10 |
| Vitamin E α-D-succinate | .1 | .001–30 |
| Flavor | 2 | .0–10 |
| Acetylsalfame K | .1 | 0–5 |

TABLE 2B

| Capsule | mg/capsule | % | Range |
| --- | --- | --- | --- |
| Cysteamine HCL | 100 | 16.7 | .001–90 |
| Vitamin E α-D-succinate | 100 | 16.7 | .001–90 |
| Magnesium phosphate tribasic | 300 | 49.9 | .001–95 |
| Mixed tocopherols | 100 | 16.7 | .001–95 |

It should be noted that Table 2B denotes a formulation of a capsule embodiment having cysteamine in the delivery system, wherein the cysteamine will buffer acid hydrolysis in the gut. In the noted embodiment of Table 2A, an alkaline earth salt-magnesium phosphate tribasic is used. However, and as is appreciated by those skilled in the art, other alkali buffers may be used.

A further pathway to increase levels of cysteamine, and thereby inhibit somatostatin, involves pantothenic acid. Pantothenic acid is a naturally occurring vitamin that is converted in mammals to coenzyme A, a substance vital to many physiological reactions. Cysteamine is a component of coenzyme A, and increasing coenzyme A levels results in increased levels of circulating cysteamine. Alkali metal salts, such as magnesium phosphate tribasic and magnesium sulphite (Epsom salts), enhance formation of coenzyme A. Furthermore, breakdown of coenzyme A to cysteamine is enhanced by the presence of a reducing agent, such as citric acid. Thus, the combination of pantothenic acid and alkali metal salts results in increased coenzyme A production and, concomitantly, cysteamine, thereby resulting in a decrease in somatostatin production. This occurs rapidly (e.g., less than 14 days) with continued administration. This, in conjunction with an increase in cholinergic tone, results in increased levels of growth hormone and cholecystokinin, with a resultant increase in lean body mass and a decrease in appetite. A representative formula containing such components and concentration ranges for the same is disclosed in Table 2C, which may be administered at a dosage of, for example, two capsules three times daily, or three capsules twice daily.

TABLE 2C

REPRESENTATIVE FORMULA

| | Mg/capsule | % | Range |
| --- | --- | --- | --- |
| Pantothenic Acid (calcium pantothenate) | 500 mg | 56 | .01–99 |
| Magnesium Phosphate Tribasic | 200 mg | 22 | .1–85 |
| Magnesium Sulfite | 100 | 11 | .1–85 |
| Citric Acid | 100 | 11 | .01–95 |

Administration of both parts of the kit of this invention to a warm-blooded animal achieves a number of beneficial results. First, the above kit is an orally administered formulation, which represents a significant improvement over existing, non-oral administration routs. As noted above, the kit of this invention serves to enhance growth hormone production, and enhance release of growth hormone by increasing cholinergic tone. In addition, by inhibiting somatostatin, both production and release of growth hormone are enhanced. Thus, an important aspect of this invention is the ability to both increase growth hormone production and release, and simultaneously antagonize an inhibitor of the same (i.e., somatostatin), and to achieve these results by an orally available route.

In the practice of this invention, it has also been found that administration of the disclosed composition results in appetite suppression. Although not intending to be limited by the following theory, it is believed that cysteamine and its various salts induces the release of cholecystokinin (CCK). This peptide is among the most powerful of all appetite suppressants (at least in humans). Therefore, it is believed that because cysteamine promotes the secretion of CCK, administration of cysteamine results in appetite suppression.

With regard to the administration of the kit, each part of the kit is, in one embodiment, administered simultaneously. For example, when both parts are in the form of a pill, capsule, tablet, liquid or the like, both parts may be taken successively—that is, at the same time or one after the other. Alternatively, administration of each part may be performed at different times. such as minutes or even hours apart. However, for convenience of administration, both parts are typically administered successively.

For purposes of illustration and not limitation, the following example more specifically disclose various aspects of the present invention.

EXAMPLE

Five normal individuals were evaluated for their IGF-1 levels by standard techniques. They were also weighed, but given no instruction to change their diet. They were then given the Formula as noted in Tables 1 and 2 for one month. Their IGF-I levels were re-evaluated and they were again weighed. Surprisingly, all of the individuals lost weight as noted in Table 4, and all had increased levels of IGF-1. As noted in Table 3, this occurred without any changes in diet or exercise.

TABLE 3

IGF LEVELS

| | Before | After |
| --- | --- | --- |
| Subject 1–50 year old male | 185 | 236 |
| Subject 2–32 year old female | 220 | 263 |
| Subject 3–66 year old male | 140 | 209 |
| Subject 4–72 year old female | 108 | 180 |
| Subject 5–36 year old male | 270 | 312 |

TABLE 4

WEIGHT

| | Before | After |
| --- | --- | --- |
| Subject 1–50 year old male | 215 | 205 |
| Subject 2–32 year old female | 142 | 133 |
| Subject 3–66 year old male | 187 | 178 |
| Subject 4–72 year old female | 160 | 154 |
| Subject 5–36 year old male | 178 | 169 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A kit for effecting weight loss in a subject in need thereof, comprising compositions A and B, wherein A and B are representative of the respective compositions, wherein A comprises an effective amount of a first composition that increases cholinergic tone and growth hormone synthesis, and wherein B comprises an effective amount of a second composition that inhibits somatostatin, wherein the first composition, A, comprises:

Choline bitartrate in an amount ranging from 0.01 to 98% by weight of the first composition;

Dimethylamino in an amount ranging from 0.01 to 85% by weight of the first composition;

Vitamin E α-D-succinate in an amount ranging from 0.01 to 85% by weight of the first composition;

Gingko biloba containing 24% ginkosides in an amount ranging from 0.001 to 30% by weight of the first composition;

St. John's Wort containing 0.3% hypericum in an amount ranging from 0.001 to 30% by weight of the first composition;

Huperzine A in an amount ranging from 0.000000001 to 5% by weight of the first composition; and 5-Hydroxytryptophan in an amount ranging from 0.001 to 30% by weight of the first composition.

2. The kit according to claim 1 wherein the second composition, B, comprises:

Cysteamine HCL in an amount ranging from 0.001 to 90% by weight of the second composition; and vitamin E α-D-succinate in an amount ranging from 0.001 to 90% by weight of the second composition.

3. A kit for effecting weight loss in a subject in need thereof, comprising compositions A and B, wherein A and B are representative of the respective compositions, wherein A comprises an effective amount of a first composition that increases cholinergic tone and growth hormone synthesis, and wherein B, comprises an effective amount of a second composition that inhibits somatostatin, and wherein the second composition, B, comprises:

Calcium pantothenate in an amount ranging from 0.01 to 99% by weight of the second composition;

Magnesium phosphate tribasic in an amount ranging from 0.1 to 85% by weight of the second composition;

Magnesium sulfite in an amount ranging from 0.1 to 85% by weight of the second composition; and Citric acid in an amount ranging from 0.1 to 95% by weight of the second composition.

4. The kit according to claim 3 wherein the first composition, A, comprises:

Choline bitartrate in an amount ranging from 0.01 to 98% by weight of the first composition;

Dimethylaminoethanol in an amount ranging from 0.01 to 85% by weight of the first composition;

Vitamin E α-D-succinate in an amount ranging from 0.01 to 85% by weight of the first composition;

Gingko biloba containing 24% ginkosides in an amount ranging from 0.001 to 30% by weight of the first composition;

St. John's Wort (0.3% hypericum) in an amount ranging from 0.001 to 30% by weight of the first composition;

Huperzine A in an amount ranging from 0.000000001 to 5% by weight of the first composition; and 5-Hydroxytryptophan in an amount ranging from 0.001 to 30% by weight of the first composition.

* * * * *